US00PP09906P

United States Patent [19]

Jones

[11] Patent Number: Plant 9,906

[45] Date of Patent: Jun. 3, 1997

[54] BLACK WALNUT TREE NAMED HPC-148

[75] Inventor: James E. Jones, Stockton, Mo.

[73] Assignee: Hammons Products, Stockton, Mo.

[21] Appl. No.: 617,047

[22] Filed: Mar. 18, 1996

[51] Int. Cl.[6] ..... A01H 5/00

[52] U.S. Cl. ..... Plt./32

[58] Field of Search ..... Plt./32

*Primary Examiner*—James R. Feyrer

*Attorney, Agent, or Firm*—Dressler, Rockey, Milnamow & Katz

[57] ABSTRACT

A new and distinct cultivar of American black walnut (*Juglans nigra* L.) That is large compared to other black walnut trees, is strong and resistant to ice and wind damage, appears resistant to many foliar diseases and is an excellent nut producer.

6 Drawing Sheets

BACKGROUND OF THE INVENTION

This invention relates to a new and distinct variety of American black walnut tree (*Juglans nigra* L.).

In 1975, I planted a variety of seedlings that I obtained from the Missouri State Nursery in Licking along with some additional seedlings I had in a plantation in Cedar County, Mo. The seedlings I obtained from the Missouri State Nursery were approximately one year old and were labeled as "super seedlings" or "nursery run". As the trees developed and began to bear fruit, I recognized that the parent tree of this invention had improved characteristics. My interest and experience with American black walnut trees led me to realize that this tree was a unique and distinct development.

REPRODUCTION

Subsequently in 1989, I asexually reproduced the tree of the present invention taking scions from the parent tree and grafting these on to an unpatented American black walnut tree root stock in Cedar County, Mo. The asexual reproductions ran true to the parent tree and to each other in all respects.

The botanical details of this new and distinct variety of American black walnut tree will now be described using data collected for the parent tree over a significant period of time.

DETAILED DESCRIPTION OF THE INVENTION

Figure 1:
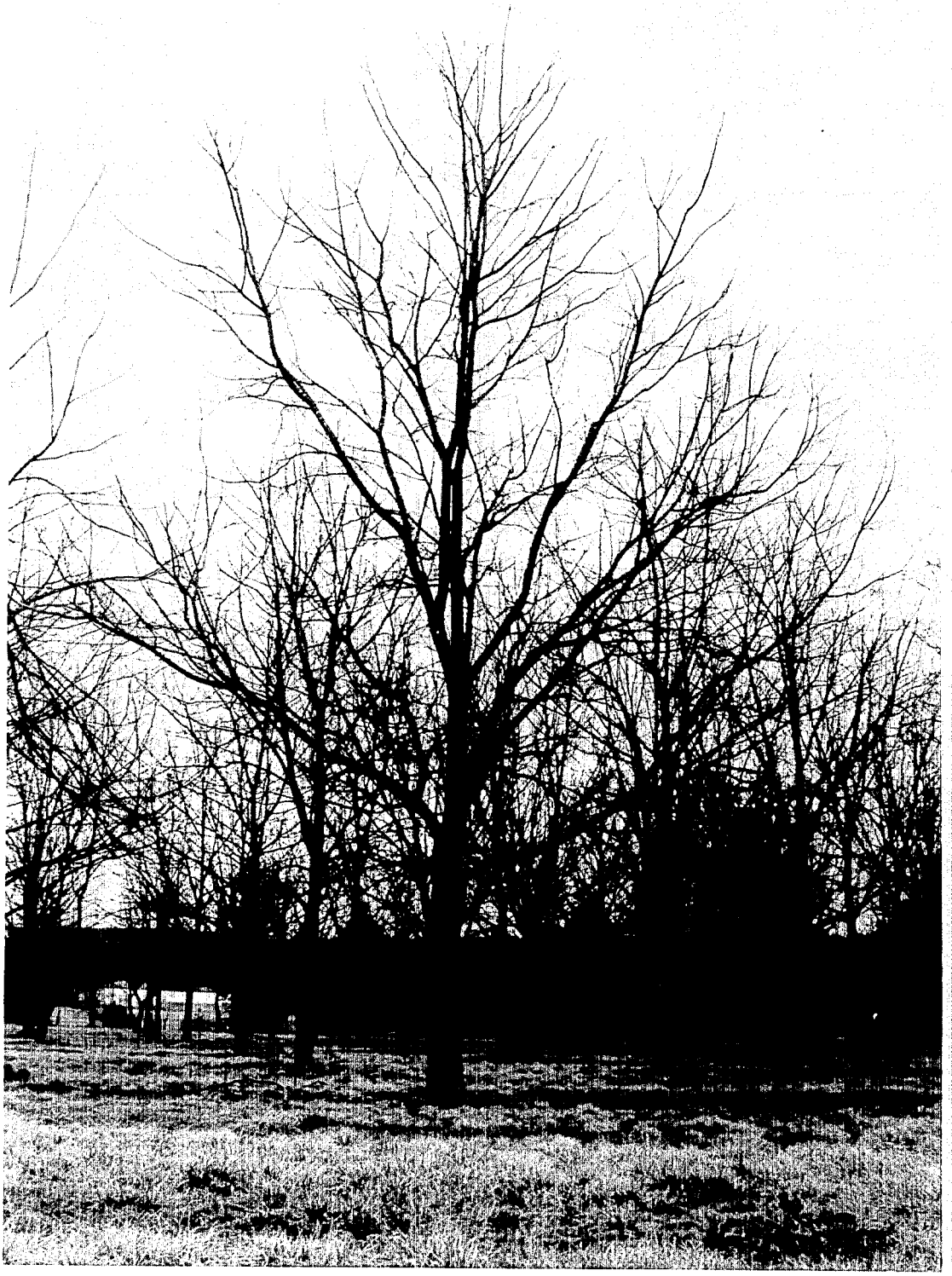
FIG. 1 is a photograph showing the timber form of parent tree of this invention at age 21.
Figure 2:
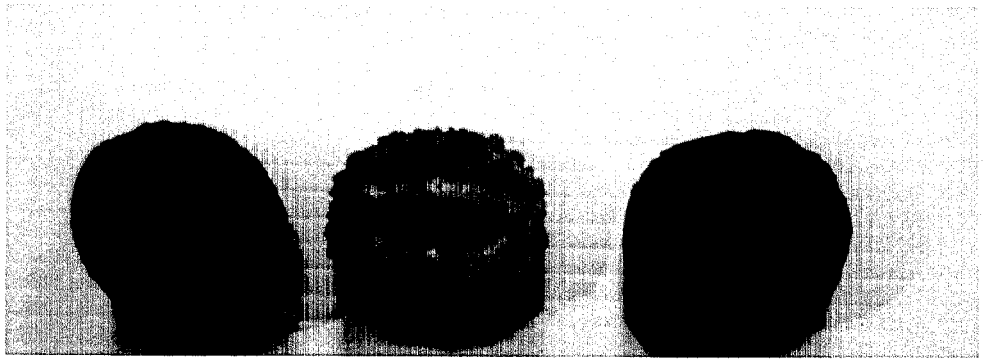
FIG. 2 is a photograph showing the nuts from the parent tree of this invention.

Tree: The tree is large when compared to other black walnut trees of this species and has a fairly well developed open grown crown. The tree exhibits modest growth and is very productive. Additionally the tree is well formed and is approximately 42 feet high, has a diameter of 11.5 inches diameter at breast height (dbh) and a spread of approximately 33 feet. The tree produces annually and has good leaf retention late into the growing season. Finally, the tree is strong and resistant to wind and ice damage.

Trunk: The trunk of the tree is like that of other black walnut trees of this species. The bark is grooved and fissured and has a lacy pattern that tends to be gray in color. The old bark is gray in color and has a grooved, interwoven and lacy texture with a thickness of approximately 1 inch. In contrast, the new bark is light brown to gray in color, has a fairly smooth texture and is approximately ¼ inches thick.

Branches: The form of the branches is the same as other black walnut trees of this species. The tree does not have any bad branch angles. The branches have a relatively smooth texture.

Stems: The stems are like the stems of other black walnut trees of this species. The stems have very short hair and are light brown to gray in color and are like the stems of other black walnut trees of this species. The internode length varies depending upon the growing season and crop size. Additionally, there is some tendency for the branches to develop and/or retain spurs (short productive twigs).

Leaves: The tree has an abundant quantity of leaves which are arranged in a pinnately compound fashion. The leaves are approximately 40 to 48 cm in length and approximately 11 to 16 cm in width. There are approximately 14 – 16 dark green leaflets per leaf which have a light pubescence on the bottom and are approximately 6 to 10 cm in length and 2.5 to 3.0 cm in width. While the leaflets are lanceolate in shape, they are pointed at the apices and somewhat round to pointed at the base. In addition, the leaflets have a smooth texture with a serrated margin and venation typical of that found in black walnut trees of this species. Normally, the centrally located leaflet is the longest. Finally, the leaflets change colors from dark green to yellow in the fall.

Leafing date: April 25 through May 5.

Inflorescence: The tree is precocious. Pistillate and staminate flowers are usually produced early, within 8 to 10 years. One to four Pistillate flowers are present per bearing site on the flowering tip. The female flower is not inconspicuous. The first female bloom is between May 1 – May 6. The peak female bloom is between May 5 – May 12. The last female bloom is between May 12 – May 21. The first male bloom is between April 26 – May 1. The peak male bloom is between April 30 – May 5. The last male bloom is May 6 – May 10. The first pollen is shed between April 30 – May 3. Generally, the pollen is shed for approximately 7 days. The last pollen shed is May 6 – May 10. The length of the female flower is ⅜ – ½ inch and the length of the male flower is 2½ – 3 inches.

Husk: The husk is generally globe-like in shape, has no suture and varies in thickness from year to year. However, the variation in husk thickness is not extreme. The surface texture of the husk is smooth and firm and has occasional dark spots. Prior to harvest, the husk is dark green in color. At harvest, the husk may be dark to light green to mottled green, brown and yellow in color. The husk does not open freely and does not have a splitting tendency. The nut with the husk in tact, is approximately 2 – 2¼ inches in length and 2 – 2¼ inches in diameter.

Figure 3:
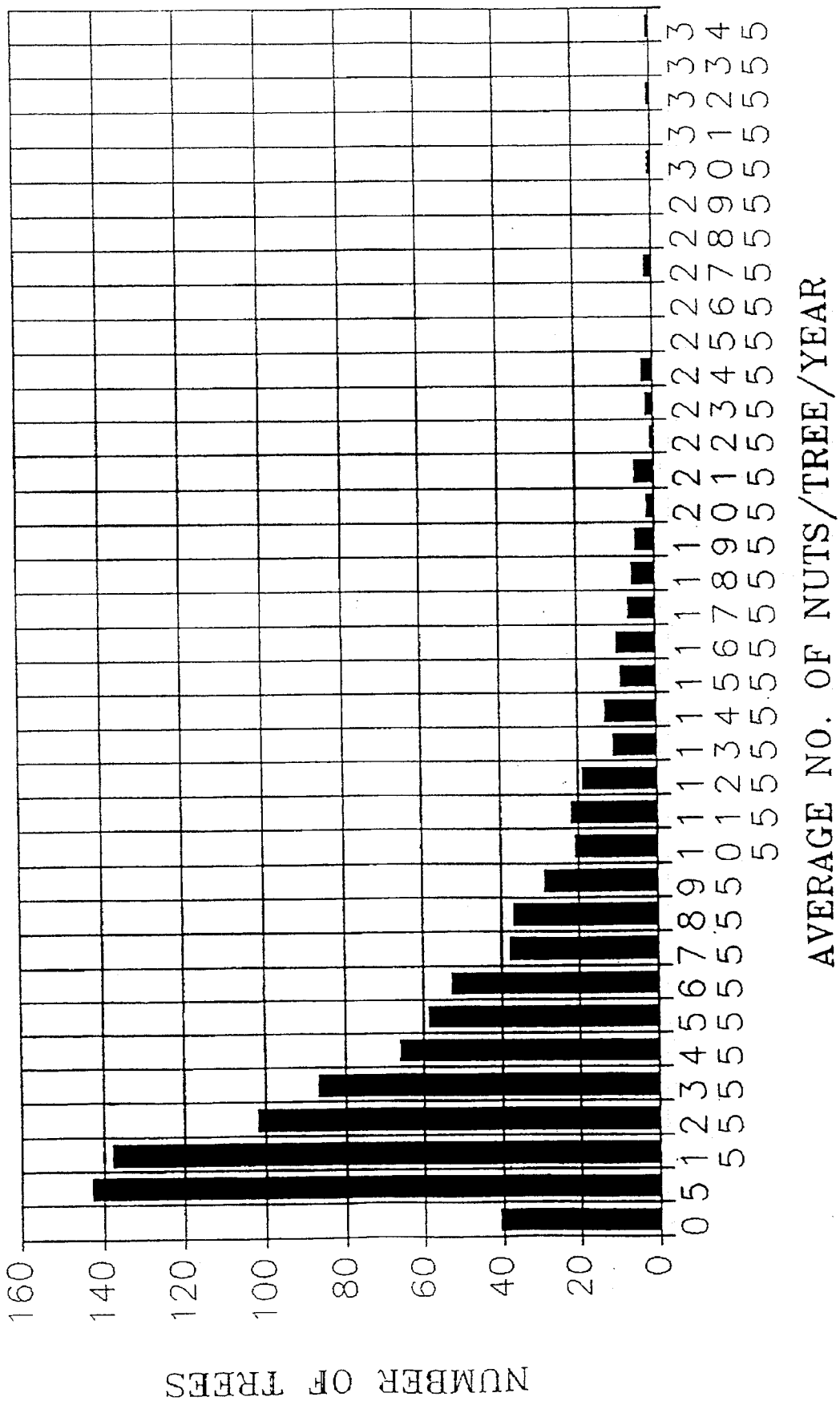
FIG. 3 is a bar graph of the walnut bearing characteristic of the parent tree of of this invention with 933 other black walnut trees grown in the same block/area.

Nut: The nut is medium in size and has an average length of 1⁷⁄₁₆ inches and an average width of approximately 1½ inches from cheek to cheek and 1¼ inches from suture to suture. The average weight of the nut is 16.6 grams and the number of nuts per ounce is 0.6. While the nut is rectangular in shape with end extensions, it is not deeply fissured and can somewhat easily be cleaned. Also, the nut is light brown to tan in color and has an inner shell and outer shell. The shell is relatively thin and the nut meat cavity is smooth and open, which enables the nutmeat to be more easily extracted from the shell. The interior of the shell does not have any irregular crevices that cause the nut meat to fragment when the shell is opened. The percentage of kernel to nut is 26.5%. FIG. 3 depicts all of the trees growing in the block/area where the parent tree of this invention is growing. These trees were grown on upland, sandstone derived soil and spaced 20'×40' apart from one another. These black walnut trees were planted in 1975 at Hammons Sho-Neff Plantation in Stockton, Mo. FIG. 3 illustrates the huge variation in nut bearing capabilities of the species. The parent tree of this invention is represented by the short vertical bar on the far right side of the graph, and produces an average of 345 nuts per year (the nuts were harvested from 1983 – 1990).

Kernel: The kernel is medium in size and has well developed lobes. The lobe has an average length of 2.0 cm, an average width of 1.5 cm and an average thickness of 0.6 – 0.8 cm. The kernel is very light brown to tan in color and has a smooth and uniform texture which facilitates its good separation from the shell. The average weight of a kernel in a nut is 5.3 grams.

Harvest: The nuts are generally ready for harvest between September 30 – October 10. No special conditions are needed for harvesting. The nuts are simply picked up by hand as they mature and fall to the ground naturally. Once harvested, the nuts are counted and the husks removed. The nuts are weighed and then air dried.

Disease resistance: The tree retains its leaves late into the growing season and appears to be resistant to many foliar diseases.

Growing conditions: Upland, sandstone derived soil. Barco soil series.

Isoelectric focusing: Isoelectric focusing was conducted on the parent tree of this invention as well as the parent tree of HPC-120 (U.S. Ser. No. 08/618,280) and STW-13 (U.S. Ser. No. 08/617,625) by Isolab, Inc., Akron, Ohio, to develop an enzyme profile for these trees. The procedure used is described below.

*Sample preparation.*—Ten individual leaves from the parent tree was homogenized with an enzyme extraction solution. The samples were allowed to incubate at 4° – 8° C. overnight. The samples were then centrifuged and the resulting supernant was ready for electrophoresis in a pH gradient.

*Isoelectric focusing.*—The supernant was run through a broad-ranged (pH 3 – 10) HyPure Gel (Isolab, Inc., Akron, Ohio). After protein separation, isozyme staining was performed for selected proteins. The stains used were selective for the following 8 enzymes: acid phosphatase, malic enzyme, diaphorase, esterase, alcohol dehydrogenase, isocitric dehydrogenase, malate dehydrogenase and peroxidase. These enzymes were selected because they are useful for showing the differences between varieties. Acid phosphatase, malic enzyme and diaphorase were chosen for further examination because these three enzymes gave the most intensity.

Results

Figure 4:
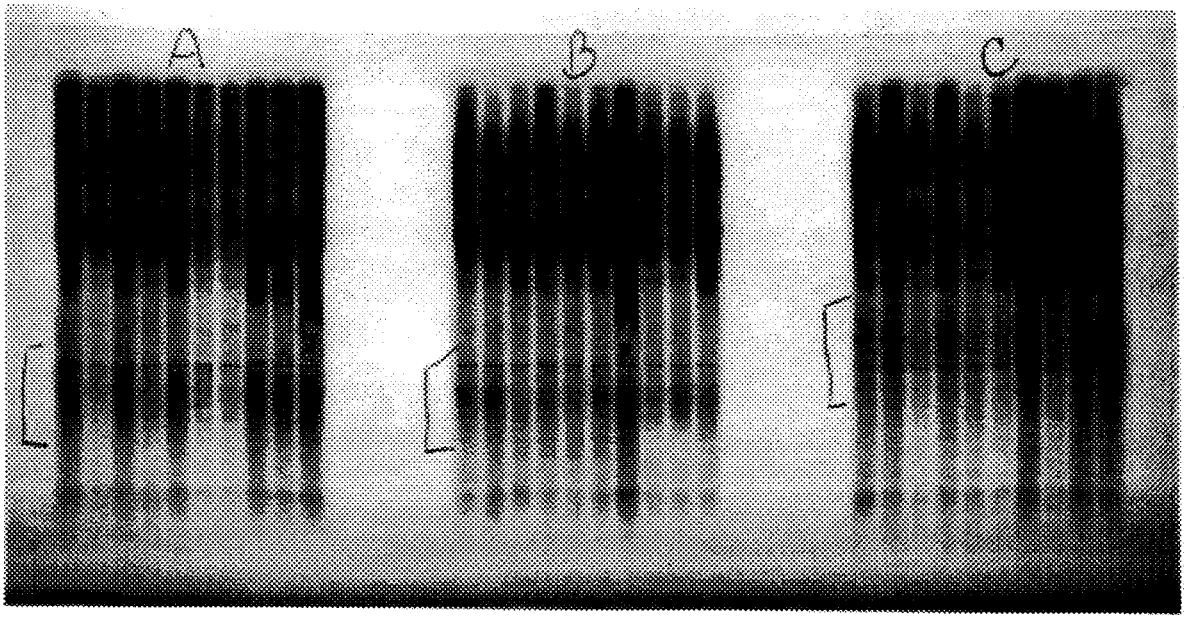
FIG. 4 contains three electrophoresis gels resulting from isoelectric focusing. The enzyme acid phosphatase was used to establish an enzyme pattern for the parent tree of this invention and other trees.

As shown in FIG. 4, the parent tree of this invention and the parent tree of HPC-120 gave the same pattern for the acid phosphatase. The parent tree of STW-13 gave a different pattern. The parent tree of this invention is shown in A, HPC-120 is shown in B and STW-13 is shown in C. Each lane represents an individual leaf sample.

Figure 5:
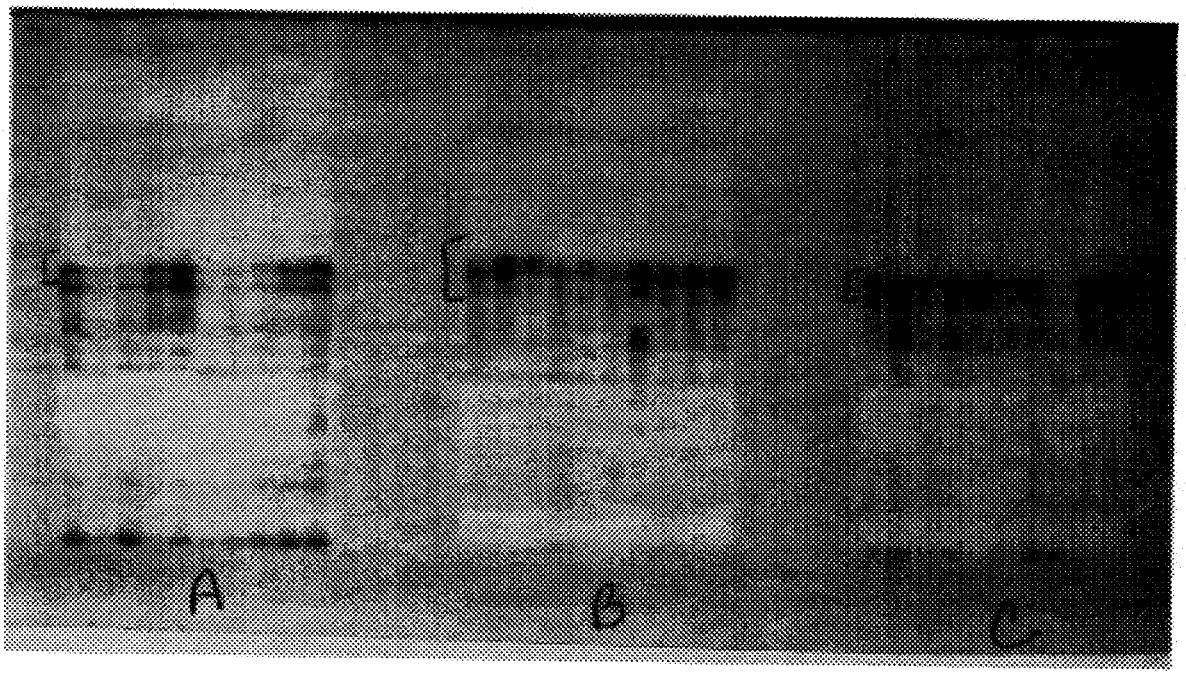
FIG. 5 contains three electrophoresis gels resulting from isoelectric focusing. The enzyme used was the malic enzyme.

As shown in FIG. 5, the parent tree of this invention and the parent tree of STW-13 gave single pattern when tested with the malic enzyme. The parent tree of HPC-120 gave a double pattern. The parent tree of this invention is shown in A, HPC-120 is shown in B and STW-13 is shown in C.

Figure 6:
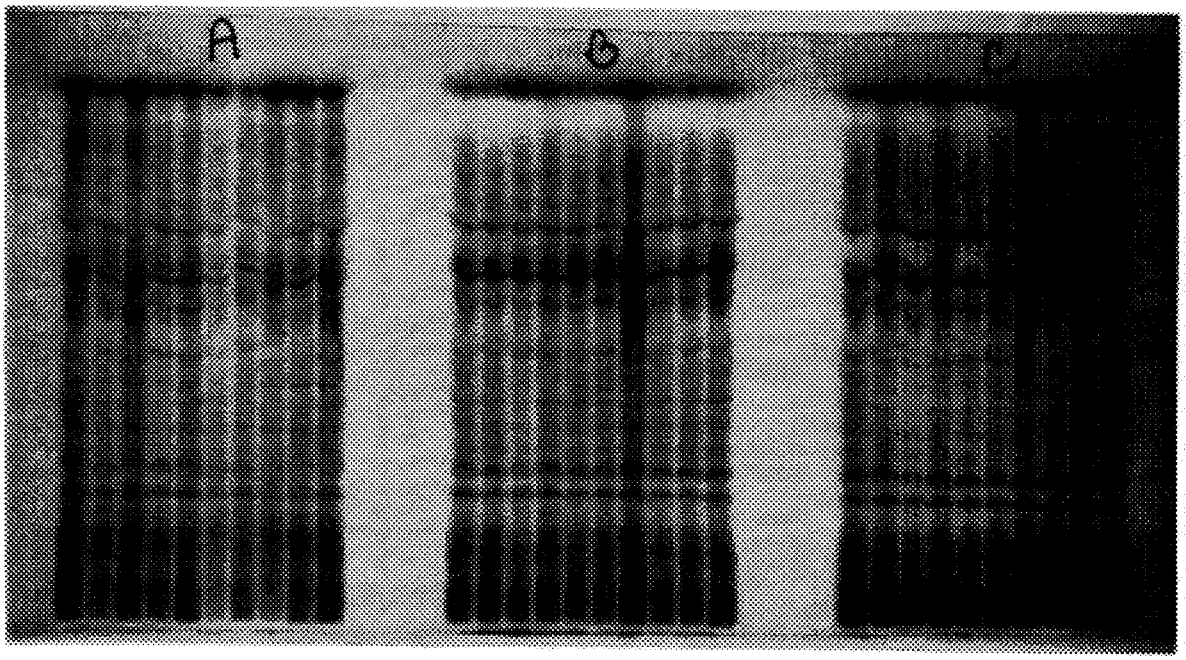
FIG. 6 contains three electrophoresis gels resulting from isoelectric focusing. The enzyme used was diaphorase.

As shown in FIG. 6, all of the trees gave the same exact enzyme pattern with for the diaphorase. The parent tree of this invention is shown in A, HPC-120 is shown in B and STW-13 is shown in C.

Therefore, these three trees can be differentiated using the acid phosphatase and the malic enzyme patterns.

I claim:

1. The new and distinct variety of black walnut tree herein described and illustrated and identified by the characteristics enumerated above.

* * * * *

AVERAGE NO. OF NUTS/TREE/YEAR
NUMBER OF TREES
0
20
40
60
80
100
120
140
160